United States Patent
Hayles et al.

(10) Patent No.: US 7,845,245 B2
(45) Date of Patent: Dec. 7, 2010

(54) METHOD FOR ATTACHING A SAMPLE TO A MANIPULATOR BY MELTING AND THEN FREEZING PART OF SAID SAMPLE

(75) Inventors: Michael Frederick Hayles, Eindhoven (NL); Uwe Luecken, Eindhoven (NL)

(73) Assignee: FEI Company, Hillsboro, OR (US)

( * ) Notice: Subject to any disclaimer, the term of this patent is extended or adjusted under 35 U.S.C. 154(b) by 424 days.

(21) Appl. No.: 12/163,298

(22) Filed: Jun. 27, 2008

(65) Prior Publication Data

US 2009/0000400 A1  Jan. 1, 2009

(30) Foreign Application Priority Data

Jun. 29, 2007  (EP) .................. 07111419
Jun. 29, 2007  (EP) .................. 07111430

(51) Int. Cl.
*B01L 3/00* (2006.01)
*G01N 1/22* (2006.01)
*G01F 23/00* (2006.01)

(52) U.S. Cl. ............. 73/864.91; 73/863.12; 250/440.11

(58) Field of Classification Search .............. 73/864.91, 73/863.11, 863.12; 250/440.11, 442.11
See application file for complete search history.

(56) References Cited

U.S. PATENT DOCUMENTS

| 5,009,743 A | 4/1991 | Swann |
| 5,270,552 A | 12/1993 | Ohnishi et al. |
| 5,986,270 A | 11/1999 | Bormans et al. |

(Continued)

FOREIGN PATENT DOCUMENTS

EP   1612836   1/2006

(Continued)

OTHER PUBLICATIONS

Matias, R.F. et al., "Cyro-Transmission Electron Microscopy of Frozen-Hydrated Sections of *Escherichia coli* and *Pseudomonas Aeruginosa*," Journal of Bacteriology, Oct. 2003, pp. 6112-6118, vol. 185, No. 20.

(Continued)

*Primary Examiner*—Hezron Williams
*Assistant Examiner*—Nathaniel Kolb
(74) *Attorney, Agent, or Firm*—Scheinberg & Griner, LLP; Michael O. Scheinberg; David Griner (57) ABSTRACT

The invention relates to the extraction of a frozen hydrated sample for TEM (Transmission Electron Microscope) inspection, such as a vitrified biological sample, from a substrate and the attaching of said sample to a manipulator. Such a hydrated sample should be held at a cryogenic temperature to avoid ice formation. By melting or sublimating a part of the sample material outside the area to be studied in the TEM and freezing the material to the manipulator (10), a bond is formed between sample (1) and manipulator. This makes it possible to transport the sample from the substrate to e.g. a TEM grid.

In a preferred embodiment a part (2) of the manipulator (10) is held at a cryogenic temperature, and the melting or sublimation is caused by heating the tip (3) of the manipulator by electric heating of the tip and then cooling the tip of the manipulator to a cryogenic temperature, thereby freezing the sample (1) to the manipulator.

20 Claims, 6 Drawing Sheets

U.S. PATENT DOCUMENTS

| | | | |
|---|---|---|---|
| 6,420,722 B2 | 7/2002 | Moore et al. | |
| 6,538,254 B1 | 3/2003 | Tomimatsu et al. | |
| 6,570,170 B2 | 5/2003 | Moore | |
| 6,664,552 B2 | 12/2003 | Shichi et al. | |
| 6,686,598 B1 | 2/2004 | Walther | |
| 6,781,125 B2 | 8/2004 | Tokuda et al. | |
| 6,870,161 B2 | 3/2005 | Adachi et al. | |
| 6,927,391 B2 | 8/2005 | Tokuda et al. | |
| 7,005,636 B2 | 2/2006 | Tappel | |
| 7,138,627 B1* | 11/2006 | Nakayama et al. | 250/306 |
| 7,381,971 B2 | 6/2008 | Moore et al. | |
| 2005/0178980 A1* | 8/2005 | Skidmore et al. | 250/492.21 |
| 2006/0017016 A1 | 1/2006 | Tappel | |
| 2006/0157341 A1 | 7/2006 | Fujii | |
| 2006/0169918 A1* | 8/2006 | Ueno | 250/443.1 |

FOREIGN PATENT DOCUMENTS

| | | |
|---|---|---|
| EP | 2009421 | 12/2008 |
| NL | 1023657 | 12/2004 |
| WO | 2006036771 | 4/2006 |
| WO | 2008051880 | 5/2008 |

OTHER PUBLICATIONS

Al-Amoudi, A. et al., "An Oscillating Cyro-Knife Reduces Cutting-Induced Deformation of Vitreous Ultrathin Sections," Journal of Microscopy, Oct. 2003, pp. 26-33, vol. 212, Part 1.

Moberlynchan, W.J. et al., "Cyro-FIB for Thinning Cryo-TEM Samples and Evading Ice During Cyro-Transfer," Microsc. Microanal., 2005, 2 pages, vol. 11, Supplement 2.

Marko M. et al., "Focused Ion Beam Milling of Vitreous Water: Prospects for an Alternative to Cryo-Ultramicrotomy of Frozen-Hydrated Biological Samples," Journal of Microscopy, Apr. 2006, pp. 42-47, vol. 222.

* cited by examiner

METHOD FOR ATTACHING A SAMPLE TO A MANIPULATOR BY MELTING AND THEN FREEZING PART OF SAID SAMPLE

TECHNICAL FIELD OF THE INVENTION

The invention relates to a method for extracting a sample from a substrate and attaching the sample to a manipulator, the method comprising the steps of: freeing at least partly a sample from a substrate, contacting the sample with the manipulator, attaching the sample to the manipulator, and removing the sample from the substrate.

The invention further relates to an apparatus equipped to perform the method according to the invention.

BACKGROUND OF THE INVENTION

Such a method is known from U.S. Pat. No. 5,270,552. The method is used for the preparation of minute samples to be observed and/or analysed in a particle-optical apparatus such as a Transmission Electron Microscope (TEM).

As is well-known a sample to be studied in a TEM needs to be extremely thin. For organic samples, as used in biology, a thickness of up to 1 μm may be used, but for high-resolution images of biological material a thickness of less than 100 nm is preferred. For samples comprising atoms with heavier nuclei, such as semiconductor samples, a thickness of less than 100 nm, preferably less than 50 nm is commonly used.

In the known method a small sample is severed from a work piece such as a semiconductor wafer. To that end the sample is cut free from the work piece by e.g. milling with an ion beam. Before the sample is completely cut free, it is attached to a manipulator tip using e.g. IBID (Ion Beam Induced Deposition). The sample is then freed completely, and may be transported by the manipulator for further preparation and/or for analysis. As known to the person skilled in the art the further preparation may include attaching the sample to a sample carrier and severing the sample from the manipulator using the ion beam.

As known to the person skilled in the art, when studying a biological sample, such as cells or other biological tissues, in e.g. a TEM, the material must either be embedded in resin or such like, or the sample must be cooled to a cryogenic temperature. The latter is advantageous in that the biological material can be observed in a state closely resembling its natural state in the vacuum of the TEM and is not easily damaged by the electron beam used in the TEM.

The attaching of the manipulator to the sample using IBID, as disclosed in the known method, involves the admittance of a gas to the evacuated sample and irradiating the sample with a focused ion beam. The admitted gas adheres to the sample, and during the irradiation of the sample with the focused ion beam the adhered gas molecules will dissociate. Part of the dissociated molecule will form the bonding material, while the other part of the dissociated molecule will form a volatile gas and leave the surface of the sample.

A problem when using the known method with frozen samples with a cryogenic temperature is that the gasses used for IBID are frozen all over the sample. Not only will this result in a contaminated sample, that is: a sample covered with an unwanted layer, but it will also result in an unreliable bond between sample and manipulator, as at cryogenic temperatures the normally volatile products formed during the dissociation of the adhered molecules will not leave the surface of the sample and may disturb the formation of the bond.

AIM OF THE INVENTION

There is a need for a method for severing e.g. cryogenic samples from a work piece and attaching the samples to a manipulator without encountering the problem identified before.

The invention intends to provide such a method.

SUMMARY OF THE INVENTION

To that end the method according to the invention is characterized in that the sample is a frozen sample,
  the sample is attached to the manipulator by heating at least the part of the sample in contact with the manipulator, thereby causing a phase change of part of the sample material, and
  subsequent freezing said part of the sample in contact with the manipulator to the manipulator, thereby forming a bond between the sample and the manipulator.

By heating the part of the sample in contact with the manipulator and then freezing it to the manipulator a bond is formed. The cooling down may be the result of the thermal conductivity to a part of the manipulator that is kept at a cryogenic temperature, or by the part cooling towards thermal equilibrium in a cold environment, i.e. caused by cooled surfaces surrounding the sample.

It is remarked that the heating may cause melting of the material of the sample, but that this need not be the case: also evaporation and/or sublimation of the sample material may occur, followed by re-deposition/condensation of the evaporated material in the gap between sample and manipulator, resulting in a bond of the between the sample and the manipulator.

It is further remarked that the at least partly freeing of the sample from the work piece may be performed by ion milling, but also using a microtome or an ultramicrotome (when preparing e.g. biological tissue), using laser ablative milling, ion beam induced etching, electron beam induced etching, etc., etc. Freeing the sample from the manipulator may be performed in a similar way, but may comprise breaking the connection left between sample and substrate by pulling the sample loose from the substrate.

RELATED PRIOR ART

U.S. Pat. No. 6,686,598 describes a method for freezing a sample in the form of a semiconductor wafer to a manipulator in the form of a platen. In this method however a liquid is inserted between the sample and the manipulator. The sample material itself is not changing phase, and the sample material is quite hard.

International Application WO98/28776A discloses an apparatus in which a cryogenic sample grid can be attached to a cryogenic sample holder. On the cryogenic sample grid a frozen sample may be attached. The cryogenic sample holder is used to position the cryogenic sample grid with respect to particle-optical elements of said apparatus so as to inspect parts of said cryogenic sample. The positioning may comprise translation and rotation of the sample carrier.

The apparatus does not disclose a method for extracting a sample from a substrate or a method of attaching the sample, but addresses the mechanical coupling of a sample grid to a sample holder at cryogenic temperatures. The sample grid is a metallic gauze as commonly used in TEM microscopy, and attaching the sample grid to the sample holder does not involve a melt/freeze cycle. The sample material itself is not changing phase.

In "Focused ion beam milling of vitreous water: prospects for an alternative to cryo-ultramicroscopy of frozen-hydrated biological samples", M. Marko et al., Journal of Microscopy, April 2006, Vol. 222, No. 1, pages 42-47, the milling of a vitreous hydrated sample with a focused ion beam is disclosed. The milling was performed on water deposited on TEM grids, frozen by immersion in a cryogenic fluid. No transfer of the sample using a manipulator is disclosed, no freeing of a part of the sample from a substrate, nor the attachment of an already frozen sample to a manipulator.

In International Application WO2006/036771A a method is disclosed in which biological material is placed on a sample grid of a form commonly used for TEM microscopy. Grid and sample are then frozen by immersion in a cryogenic fluid, and then transferred to an electron microscope. This known method differs from the invention in that a sample grid is manipulated, and that no attaching of an already frozen sample to said grid is disclosed, nor is a melt/freeze cycle disclosed.

In European Application EP1612836 the extraction of a semiconductor sample from a substrate is disclosed where the sample, before separation from its substrate is attached to a manipulator using Ion Beam Induced Deposition (IBID). No temperature changes of the manipulator are described for attaching the sample to the manipulator, nor is melting/freezing of the sample material disclosed.

In US application US2005/178980 a method for extraction of a sample from a substrate and attaching said sample to a manipulator is disclosed, in which a malleable layer of e.g. gold, indium or such covers the manipulator. The malleable layer may be heated to soften or melt and thereby form a bond between the sample and the manipulator. This known method does not disclose that the sample material itself undergoes a phase change for attaching itself to the manipulator, nor does it disclose its use for frozen biological samples.

EMBODIMENTS

In an embodiment of the method according to the invention the sample comprises water.

The method is especially suited to be used with samples containing water, in which water is melted or evaporated/sublimated and re-frozen, thereby forming an ice bond between sample and manipulator.

In a further embodiment of the method according to the invention the sample is a vitrified sample.

A vitrified sample is frozen in such a way that the ice is amorphous. This is a process known to the person skilled in the art, involving cooling the sample so fast that ice needles have no time to form. This is a preferred method for freezing e.g. biological tissues as artefacts due to the phase change of water are avoided.

It is remarked that local re-freezing of the sample may result in a region of the sample losing its amorphous state. The region may e.g. show ice needles. However, by choosing the region where this phase change occurs (the region where the sample is attached to the manipulator) sufficiently small and sufficiently far removed from the areas of interest on the sample, it need not influence the usability of the sample.

In another embodiment of the method according to the invention the method further comprises separating the sample from the manipulator by heating at least the part of the sample in contact with the manipulator.

Often the sample must be detached from the manipulator after attaching, or at least placing, the sample on a sample holder such as a conventional TEM grid.

In a further embodiment of the method according to the invention the heating is caused by a focused beam of light.

By focusing a beam of light onto the manipulator or, alternatively, on the boundary where manipulator and sample touch, the manipulator and/or the sample is locally heated to a temperature above the temperature where the phase change occurs. By interrupting the illumination the heated part of the sample and/or the manipulator is allowed to cool down, thereby freezing the sample to the manipulator.

It is remarked that the focal spot of the beam of light is preferably small so that only a small part of the sample changes phase and a large part of the sample does not change. A laser beam may well be used to achieve such a small focal spot.

It is further remarked that the light may be focused on the sample, thereby heating the sample material, but alternatively the light may be focused on the manipulator, thereby heating the manipulator, the manipulator in turn heating the sample where sample and manipulator touch. It is also envisaged that the manipulator is heated in this way prior to contacting the sample.

In yet another embodiment of the method according to the invention the heating is caused by a beam of energetic particles.

In this embodiment focusing a beam of energetic particles, e.g. electrons, where manipulator and sample touch, causes local heating.

It is remarked that the beam may be focused on the sample, thereby heating the sample material, but alternatively the beam may be focused on the manipulator, thereby heating the manipulator, and the manipulator in turn heating the sample where sample and manipulator touch. It is also envisaged that the manipulator is heated in this way prior to contacting the sample.

In still another embodiment of the method according to the invention the heating is caused by the temperature of the part of the manipulator in contact with the sample, said temperature of the manipulator at the moment of phase change being above the temperature at which the phase change occurs.

By heating the part of the manipulator in contact with the sample to a temperature causing the material of the sample to change phase, and then allowing it to cool down again, the sample is frozen to the manipulator.

The cooling down of the part of the manipulator in contact with the sample may be the result of the thermal conductivity to a part of the manipulator that is kept at a cryogenic temperature.

In a further embodiment of the method according to the invention the temperature of the part of the manipulator in contact with the sample is changed by electric heating of said part.

The electric current that causes the electric heating may be supplied as a current flowing through a heating coil, but may also be a current flowing from a part of the manipulator through a resistive wire to the sample material, as experiments have shown that the resistivity of many samples is sufficiently low to conduct a current sufficiently high to heat such a resistive element.

In another embodiment of the method according to the invention part of the manipulator is kept at a temperature below the freezing point of the sample material.

Cooling down the heated part of the sample may be caused by thermal conductivity to a part of the manipulator that is kept at a temperature below the freezing point of the sample material.

In yet another embodiment of the method according to the invention the method is performed in vacuum.

To avoid condensation of gasses onto the cryogenic sample and/or manipulator, resulting in contamination, the method is preferable executed in a vacuum.

It is remarked that it may seem impossible to perform the method according to the invention in vacuum using e.g. water, as the phase diagram of water shows that at a pressure below approximately 6 mbar (the pressure associated with the triple point of water) solid ice changes directly to vapour, a process known as sublimation. However, experiments show the feasibility of the method in vacuum. Three mechanisms may explain this:

a very localized pressure or pressure burst in excess of 6 mbar may occur when a heated part touches the sample, said pressure sufficiently high for the ice to melt instead of to sublimate, local evaporation may results in re-deposition of the gas thus formed in the gap between the sample and the manipulator, as a result of which an ice bound is formed, or the attaching of the sample is caused by a phase change from e.g. amorphous to crystalline ice, the latter phase bonding the sample and the manipulator.

Similar alternatives are possible for other sample materials or material phases.

In still another embodiment of the method according to the invention the method further comprises inspection and/or analysis of the sample with an energetic beam of charged particles.

The method is particularly suited to prepare samples for study in an electron microscope, such as a cryo-TEM (Cryogenic Transmission Electron Microscope) or a cryo-STEM (Cryogenic Scanning Transmission Electron Microscope), after which the samples may be introduced in the cryo-TEM or cryo-STEM for inspection and/or analysis. Such preparation is often done in an apparatus that is equipped to inspect the sample with a scanning electron beam or a scanning ion beam in order to view the sample during the manufacturing of the minute samples, thereby enabling e.g. positioning and handling of the minute samples.

In a further embodiment of the method according to the invention the phase change of the sample is restricted to an area of the sample outside the area to be inspected and/or analysed.

By restricting the area that is changing phase, the formation of e.g. ice needles is limited to said area. Restricting the area may be done by heating the part of the sample a short time, and then quickly allowing it to cool down to a temperature below the glass transition temperature. Cooling down is e.g. realized by the thermal conductivity to the part of the manipulator held at a cryogenic temperature.

In another embodiment of the method according to the invention the freeing of the sample involves focused ion beam milling.

It is known that ion beam milling can be used to free a vitrified sample from a vitrified substrate without a phase change of the sample. This is described in e.g. "Focused ion beam milling of vitreous water: prospects for an alternative to cryo-ultramicroscopy of frozen-hydrated biological samples", M. Marko et al., Journal of Microscopy, April 2006, Vol. 222, No. 1, pages 42-47. Focused ion beam milling is thus a preferred method of freeing such a sample from its substrate. Ion beam milling thus enables a mechanically soft medium such as a vitrified sample that behaves as a high-viscosity fluid to be freed and manipulated while avoiding mechanical deformation in the freed sample.

In a further embodiment of the method according to the invention the freeing of the sample comprises slicing a lamella from a frozen core, the lamella representing a cross-section of said core.

By forming such a cross-section of the core, bacteria, viruses or e.g. biological tissue can be freed for further inspection in e.g. a Transmission Electron Microscope (TEM).

In a still further embodiment of the method according to the invention the core is covered with a protective layer prior to slicing the lamella from the core.

When irradiating a core with a focused ion beam, a high intensity part of the beam mills the material from the position where the focus is formed. However, also core material removed from the focus is irradiated by the beam, resulting in erosion and/or damage of the core. By covering the core with a thin layer of protective material the effect of this low-intensity part of the beam is deferred.

It is noted that the protective layer may be a liquid layer, resulting from condensation of a gas, or it may be a solid, frozen to the core from e.g. the gas phase.

In a yet further embodiment of the method according to the invention the core is covered with a protective layer by directing a jet of gas to the core while rotating the core with respect to the jet of gas.

In another embodiment of the method according to the invention the core is formed by high-pressure freezing of a hydrated material, resulting in a vitreous core.

The formation of a high-pressure frozen core is known per se and is e.g. described in Such a method is known from "Cryo-transmission Electron Microscopy of frozen-hydrated sections of *Escherichia coli* and *Pseudonomas aeruginosa*", V. R. F. Matias et al., Journal of Bacteriology, October 2003, pages 6112-6118, more specifically page 6113, section "materials and methods". Hydrated biological material comprising e.g. microbes is frozen inside a thin copper tube by high-pressure freezing. The method according to the invention is well suited to slice a lamella from the thus formed core, and attach the lamella to a manipulator.

In an aspect of the invention an apparatus for forming samples from a cryogenic hydrated substrate and attaching the samples to a manipulator, the apparatus comprising: a column equipped to produce a focused ion beam on a sample position, a stage for holding the substrate equipped to position the substrate, in which at least the part of the stage equipped to be in contact with the substrate is equipped to be cooled to a cryogenic temperature, and a manipulator showing an extremity to which extremity a sample may be attached, the extremity of the manipulator equipped to be held at a cryogenic temperature, is characterized in that the extremity of the manipulator is equipped to be heated to a temperature above the melting temperature or sublimation temperature of water while another part of the manipulator is held at a cryogenic temperature.

An apparatus according to the pre-amble is known and available from FEI Company. A cryo-FIB is also described in "Cryo-FIB for thinning Cryo-TEM samples and evading ice during cryo-transfer", W. J. Moberly Chan et al, Microsc. Microanal 11 (Suppl 2) 2005, page 854. A cryogenic sample can be introduced in the apparatus on the stage so that the sample is positioned at the sample position. As the stage is held at a cryogenic temperature.

It is noted that, as known to the person skilled in the art, the presence of so-named cryo-shields may help in keeping the sample at a cryogenic temperature.

The system is used to either observe the surface of a sample with a Scanning Electron Microscope (SEM column), or to thin a sample already placed on a TEM grid to a thickness appropriate for TEM By equipping the manipulator with an extremity that can be heated to a temperature above the melting or sublimation temperature of water, after which the extremity is cooled to a temperature below the freezing point of water, the lamella can be attached to the manipulator by freezing the (locally heated) lamella to the manipulator and thereby the before mentioned method can be performed.

In an embodiment of the apparatus according to the invention the apparatus further comprises a gas injection system to direct a jet of gas to the sample position.

This enables the application of a protective layer to a sample such as a core.

In another embodiment of the apparatus according to the invention the substrate is a core and the apparatus is further equipped with a programmable control unit controlling the apparatus in such a way that the apparatus is equipped to automatically position the core to a cutting position, cover the core with a protective coating by directing a jet of fluid to the core, slice the core, thereby forming a lamella from the core, connect the extremity of the manipulator to the lamella to transport it to a sample carrier, and release the lamella on the sample carrier.

BRIEF DESCRIPTION OF THE DRAWINGS

The invention will be elucidated on the hand of figures, whereby identical reference numerals indicate corresponding elements.

To that end.

DETAILED DESCRIPTION OF THE DRAWINGS

Figure 1:
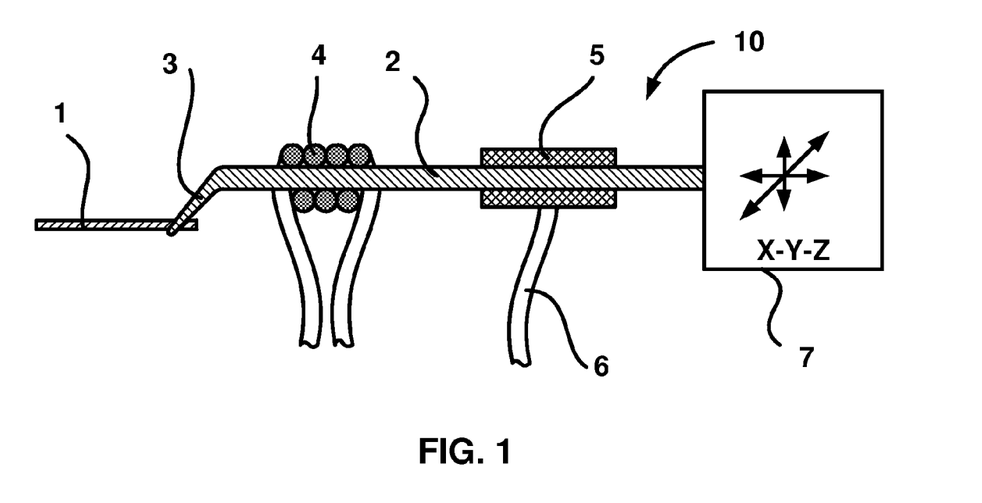
FIG. 1 schematically depicts a sample and a manipulator equipped to perform the method according to the invention, FIG. 2 schematically depicts a sample and an alternative manipulator equipped to perform the method according to the invention, FIG. 3 schematically depicts the contact area between sample and manipulator, where the contact area is heated with a particle beam, FIG. 4 schematically depicts the contact area between sample and manipulator, where the contact area is heated with a focused beam of light, FIG. 5 schematically depicts an apparatus equipped to perform the method according to the invention, FIG. 6 schematically shows a core from which a lamella is sliced and attached to the manipulator, FIG. 7 schematically shows a core that is covered with a protective layer, and FIG. 8 schematically shows an apparatus to slice a lamella from a core and deposit it on a sample carrier.

FIG. 1 schematically depicts a sample and a manipulator equipped to perform the method according to the invention.

The manipulator 10 comprises a rod 2 with a tip 3. The manipulator further comprises a movable stage 7 to which the rod is connected, which enables the tip to be positioned. In this embodiment the stage is depicted as movable along all 3 axis X-Y-Z, but also stages with less degrees of freedom (e.g. only X-Y movement) or more degrees of freedom (e.g. rotation round the X-axis) may be used. The manipulator also comprises a heating unit in the form of flexible heating wire 4 coiled around rod 2, and a cooling jacket 5 round rod 2 that is kept at cryogenic temperature via cooling wire 6. Cooling wire 6 may consist of e.g. a flexible braid of copper wire so as to form a path with high thermal conductivity to a cooling block kept at cryogenic temperature by liquid nitrogen, liquid helium or the like (cooling block not shown).

A sample 1 is placed against the tip of the manipulator.

The tip 3 of the rod 2 can be heated by passing an electric current through resistive wire 4. The tip can thereby be held at a cryogenic temperature (when no heating is applied and only cooling via cooling jacket 5 occurs) at which the material of the sample is frozen, or the tip can be held at a temperature at which the material of the sample is melted or sublimated by passing a current through heating wire 4.

It is remarked that when using an aqueous vitrified sample, to avoid re-crystallisation of the water, the sample must be kept below the re-crystallisation temperature of water, i.e. below a temperature of approximately 136 K, see e.g. "An oscillating cryo-knife reduces cutting induced deformation of vitreous ultrathin sections", A. Al-Amoudi et al., Journal of Microscopy, Volume 212 number 1 (October 2003), pages 26-33, more specifically page 26, right hand column. By cooling the copper braid with e.g. liquid nitrogen (boiling temperature approximately 70 K), such a temperature can well be achieved.

Figure 2:
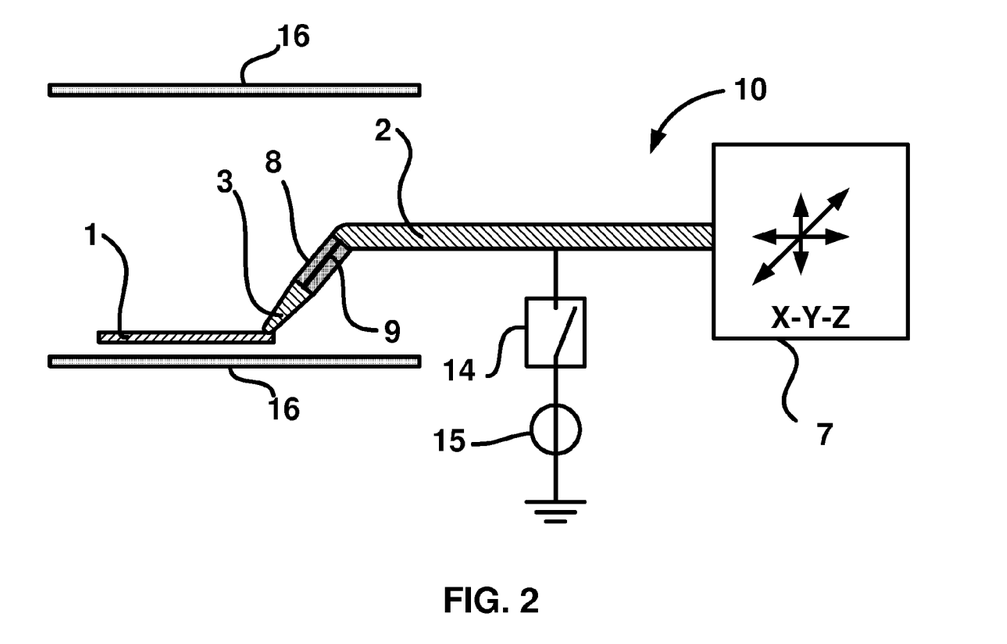

FIG. 2 schematically depicts a sample and an alternative manipulator equipped to perform the method according to the invention.

FIG. 2 shows a simpler manipulator than depicted in FIG. 1, which yields good results.

On the electrically conductive rod 2 an electrically conductive tip 3 is mounted via an electric insulator 8. Insulator 8 can be e.g. a ceramic bead or a glass bead. In the insulator a resistive wire 9 connects the tip and the rod.

The environment of the sample and the tip of the manipulator are surrounded by cryo-shields 16, which are held at a cryogenic temperature.

A voltage source 15 can be connected to rod 2 via a switch 14, thereby applying a voltage to the rod 2.

When the tip 3 is electrically contacting a part held at ground potential, and switch 14 is closed, a current passes through the rod via the resistive wire to tip 3. This will heat the resistive wire, and thereby also tip 3.

Experiments have shown that, when a sample of frozen or vitrified material is contacted by the tip, the resistance of the ice or the vitrified water is sufficiently low to cause heating of the tip. This will cause a local phase change of the sample. By then interrupting the current flowing through the resistive wire by opening switch 14, the tip will cool down due to the contact with the sample and/or by reaching an equilibrium temperature with the cryo-shields 16.

It is remarked that the tip 3 can be the end of resistive wire 9. If the wire is sufficiently stiff, then insulator 8 can also be eliminated, reducing the number of elements.

It is further remarked that by applying a voltage to rod 2 before contacting the sample and monitoring the current delivered by the voltage source, and then positioning the tip, the moment of contact between sample and tip can be determined. This in turn can trigger the end of the movement of the manipulator so that the tip and the sample just touch each other, after re-freezing resulting in a bond between the two that is not overly large. It may also trigger a timer that disconnects the voltage source from the rod after a predetermined time delay. Said triggers may be used to perform the method according to the invention automatically.

Figure 3:
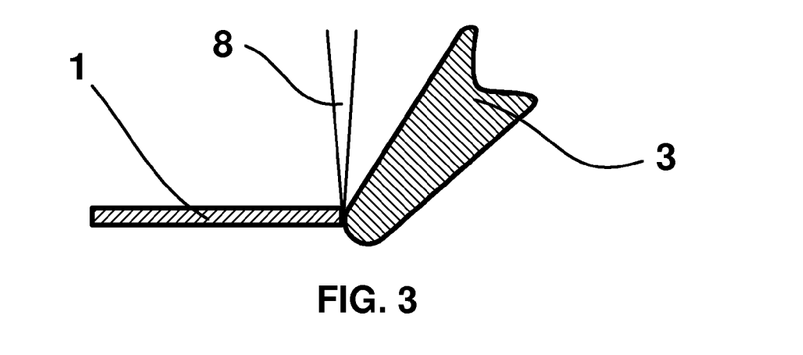

FIG. 3 schematically depicts the contact area between sample and manipulator, where the contact area is heated with a particle beam.

This figure shows only part of the sample 1 and tip 3 of the manipulator 10, and depicts another method for heating the interface between sample and tip. By focusing a particle beam, e.g. an electron beam with a voltage of 30 kV and a current of 100 nA, a power of 3 mW is focused on the interface. Although this power may seem little, the tip of the rod need not be large: the sample is typically less than 1 Mm thick and less than e.g. 0.1 mm in diameter (although samples with a larger diameter or thickness may be used). Therefore the tip can be small and sharp as well and a power in the order of 1 mW may suffice to raise the temperature of the interface to a temperature sufficiently high to melt or sublimate part of the sample.

It is remarked that in this embodiment no electric heating by resistive wire 4 (shown in FIG. 1) is used, and that this wire may thus be omitted. It is further remarked that the particle beam may heat the sample by focusing it on the sample, but that it may also heat the tip 3 of the manipulator by focusing it to the manipulator. It need not irradiate the interface itself, as long as material of the sample is melted or sublimated, e.g. by irradiating a part of the tip slightly removed from the interface.

Figure 4:
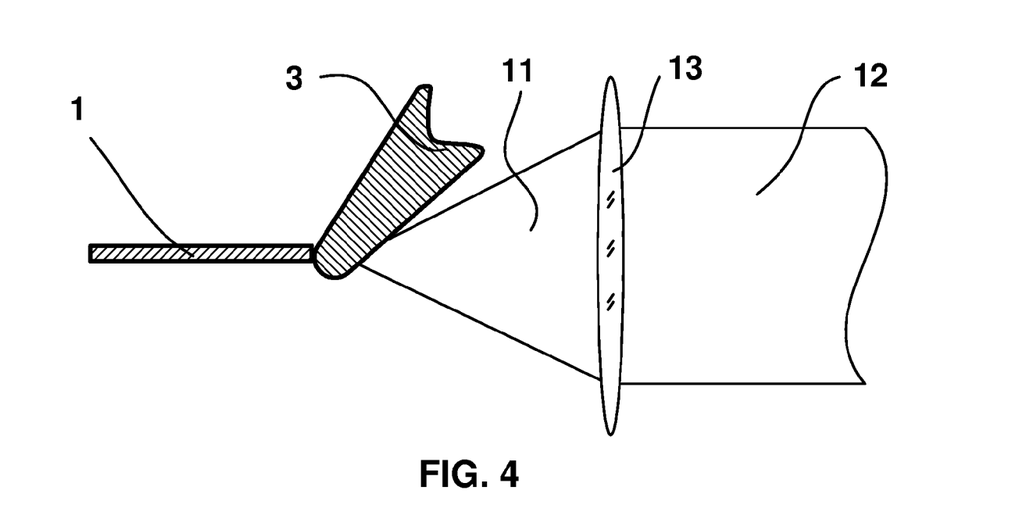

FIG. 4 schematically depicts a detail of FIG. 1, showing the contact area between sample and manipulator, where the contact area is heated with a focused beam of light.

By focusing a beam of light, such as a laser beam, the tip of the manipulator is heated. The parallel beam 12 is focused by lens 13 to form a focused beam 11 on the tip 3 of the manipulator.

It is remarked that the laser beam can be an infrared laser beam, or a laser beam using visible light.

It is further remarked that in this embodiment as well as in the embodiment of FIG. 2 resistive wire 4 (shown in FIG. 1) is not used and can be omitted.

Figure 5:
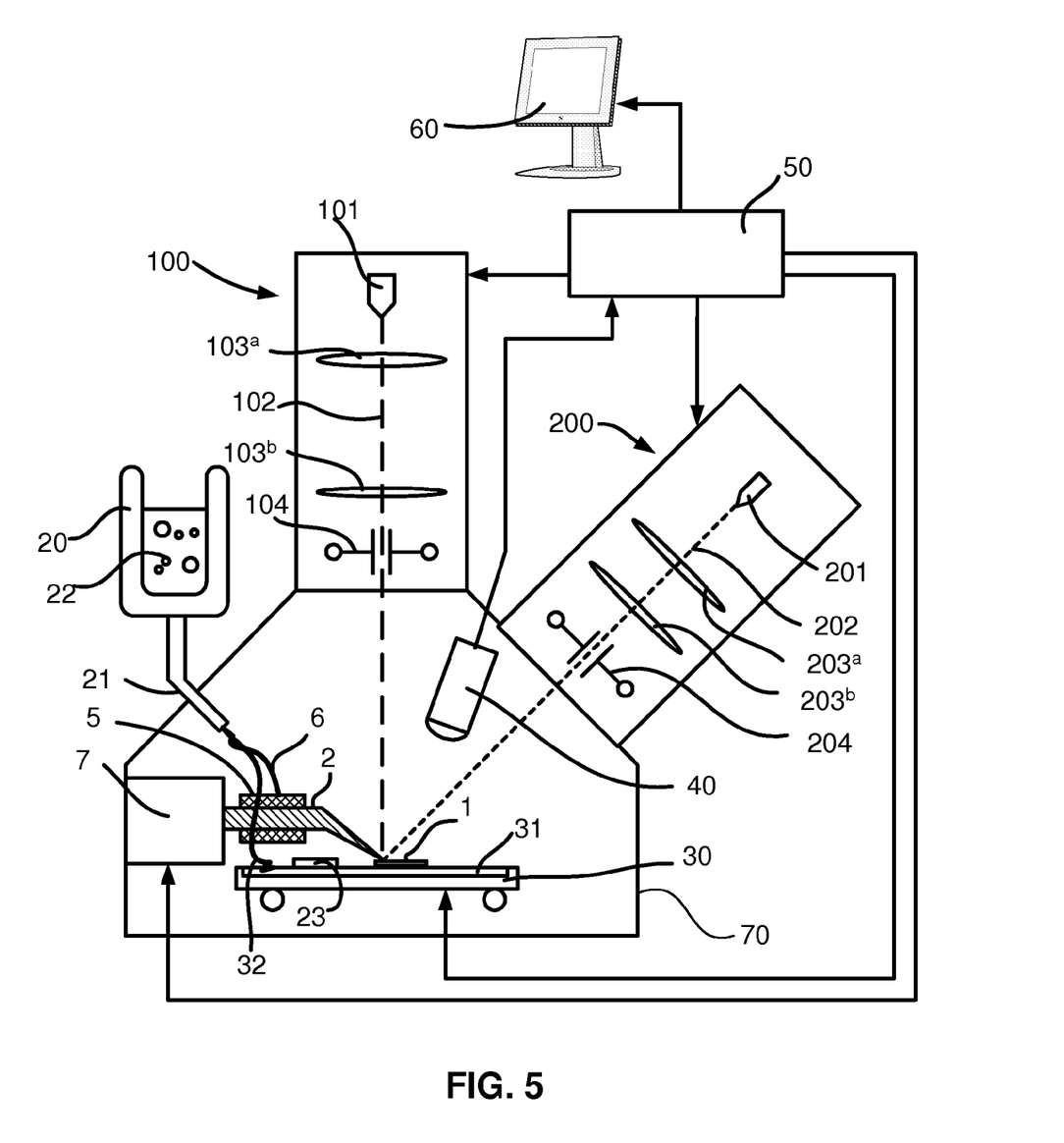

FIG. 5 schematically depicts an apparatus equipped to perform the method according to the invention.

A vacuum chamber 70 is connected to a SEM (Scanning Electron Microscope) column 100 and a FIB (Focused Ion Beam) column 200.

The SEM column 100 comprises an electron source 101 producing a beam of electrons 102. The electron beam is focused by particle optical lenses 103A and 103B, which may be electrostatic lenses or magnetic lenses. The electron beam is deflected by deflector 104.

The FIB column 200 comprises an ion source 201 producing a beam of ions 202. The ion beam is focused by particle optical lenses 203A and 203B, which are preferably electrostatic lenses, but may also be magnetic lenses. The ion beam is deflected by deflector 204.

On the vacuum chamber a dewar 20 is mounted which shows a cold finger 21 inside the vacuum. By filling the dewar with e.g. liquid nitrogen 22 the temperature of the cold finger will be close to the boiling point of liquid nitrogen. That temperature is low enough to keep a vitrified sample vitrified.

In the vicinity where both beams intersect each other a sample 1 is placed on a stage 30. Stage 30 enables positioning the sample with respect to the intersecting beams, and may be a relatively simple X-Y table, but may also offer capabilities to orient the sample with more degrees of freedom. Stage 30 comprises a platen 31 that is connected with the cold finger 21 via flexible braid of copper wire 32. Thereby platen 31 is kept at a cryogenic temperature.

Manipulator 10 is equipped with a jacket 5 surrounding a rod 2. Rod 2 is connected to a movable stage 7, so that the extremity of the rod can be positioned to be in contact with the sample. Jacket 5 is connected to the cold finger 21 via a flexible braid of copper wire 6. Thereby the jacket is kept at a cryogenic temperature, and thereby the rod 5.

Radiation in the form of e.g. secondary electrons emerging from the sample as a result of the irradiating beam or beams (102, 202) is detected by a detector 40. The signal of this detector is acquired by controller 50, said controller also controlling the columns, the scanning of the beams over the sample, the position of the stage 30 and the position of manipulator 10. Hereby an image of the sample can be displayed on monitor 60.

The vacuum chamber 70 and the interior of the columns 100 and 200 are kept evacuated. This is necessary to let the beams 102 and 202 travel from their sources 101 and 102 to the sample and to let e.g. secondary electrons from the sample to the detector 40. It also eliminates condensation of gas onto the sample.

Instruments comprising a FIB column and a SEM column are commercially available, e.g. the DualBeam® of FEI, Hillsboro, Oreg., USA. As known to the person skilled in the art a work piece such as a wafer or such as biological material can be milled with the ion beam so that a sample is freed from the work piece. With the manipulator according to the invention the sample can be attached to the manipulator 10 by a local heating of the sample and/or local heating of the manipulator, e.g. by irradiating these parts with the electron beam 102, followed by a cool down of the heated part(s). To that end the current in the beam may be larger than the current normally used for optimum resolution of an image acquired with optimum resolution. Optimum resolution at an electron beam energy of e.g. 30 keV is often achieved at a current of e.g. 1-10 pA, while a current in excess of 100 nA may be used for heating. As a result the sample will show a part in contact with the manipulator where material is melted or sublimated. Reducing the current on that part results in cooling of that part via rod 2, which is kept at a cryogenic temperature, and thus the sample 1 will freeze to the manipulator 10. Thereafter the sample can be processed further. This processing may include thinning of the sample to its final thickness and/or attaching it to a conventional TEM grid 23. For easy access the TEM grid may e.g. be positioned on the stage 30, so that the sample can be positioned on the TEM grid by positioning stage 30 accordingly and then detaching the sample from the manipulator by heating the sample. Afterwards the TEM grid may be transferred to a TEM for final inspection.

It is remarked that it is possible to extend the apparatus according to the invention with a Transmitted Electron Detector (TED), in which the electrons produced by the SEM column 100 and transmitted through the sample 1 are detected. This enables preparation and inspection of a sample in one apparatus. It can also be envisaged to observe the sample at another location in the same apparatus, enabling the inspection of one sample while freeing another one from a work piece.

Figure 6:
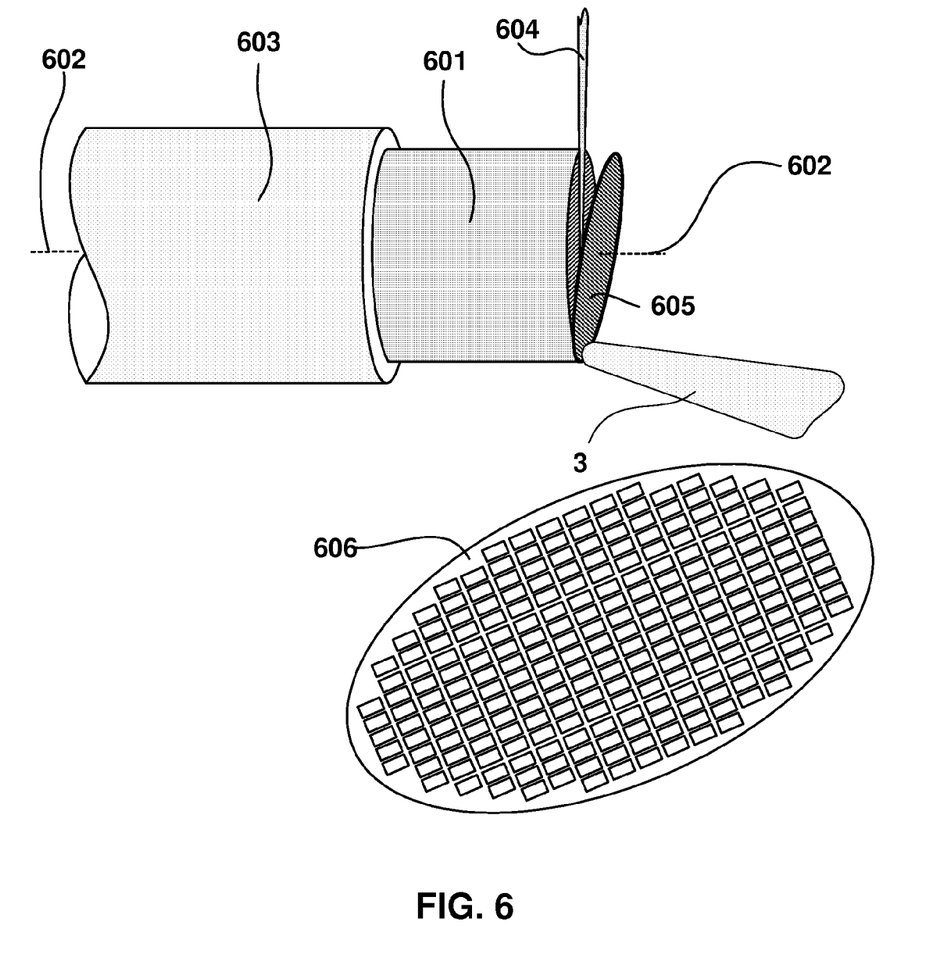

FIG. 6 schematically shows a core from which a lamella is sliced and attached to the manipulator.

A core 601 is formed in a copper tube 603 by high-pressure freezing, a method known per se. The inner diameter of the copper tube is typically between 100 and 250 μm, but tubes with different inner diameters may be used, resulting in core samples with different outer diameters. Although the term copper tube implies that a cylindrical core sample is formed, the tube need not have a circular inner cross-section and tubes with other cross-sections may be used, resulting in a core with non-circular outer cross-sections.

After forming the core by said freezing technique the core in the tube is placed in an evacuated environment. Due to the lowering of the pressure, and also due to the lowering of the temperature during the freezing, a part of the core often extends along axis 602 from the copper tube. It is also possible to squeeze a part of the core out of the tube.

A focused ion beam 604 is focused on the core 601 and thereby removes material between the core and the lamella 605. The ion beam preferably has an orientation substantially perpendicular to axis 602 along which the core extends, thereby slicing a lamella representing a perpendicular cross-section of the core. However also slicing lamella under other angles yields lamella usable for TEM inspection.

Lamella 605 is attached to extremity 3 of the manipulator by melting and subsequent freezing of the lamella to the manipulator, after which it can be placed on the sample grid 606.

It is noted that, prior to freeing a lamella fit for inspection in e.g. a TEM, it might be attractive to form a flat face on the core by milling a part from the core.

It is further noted that the traditional method of attaching a lamella to a manipulator by Ion Beam Induced Deposition (IBID), which is widely used at room temperature, is less suited for use with cryogenic lamellae, as the gasses used behave differently at cryogenic temperatures, resulting in e.g. condensation all over core sample, lamella and manipulator. Also the chemistry of IBID differs at cryogenic temperatures, as a result of which the normally volatile gasses formed during IBID will not evaporate.

Figure 7:
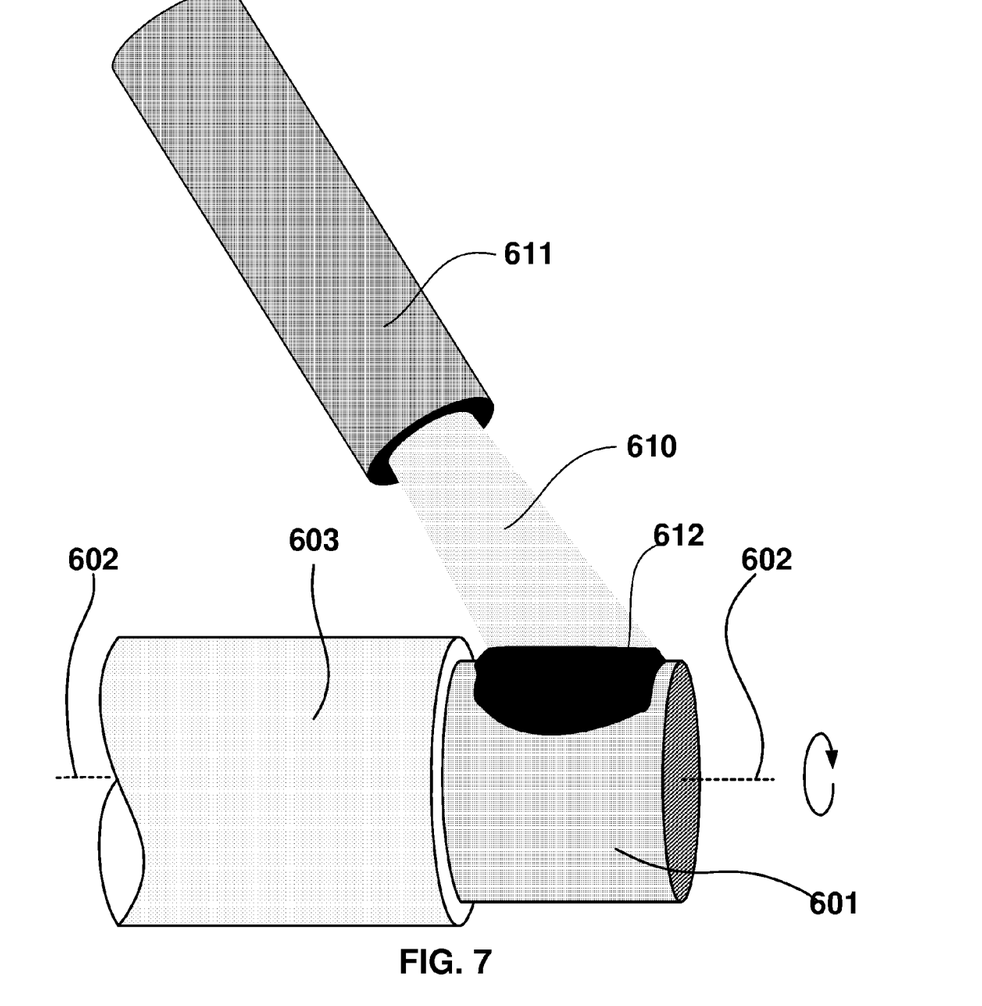

FIG. 7 schematically shows a core that is covered with a protective layer.

A gas nozzle 611 directs a jet of a fluid 610 towards the core 601. The fluid condenses on the core in a protective layer 612. Said protective layer may be a liquid layer, or it may be frozen to a solid. By rotating the copper tube 603 and the core 601 round axis 602, the core sample can be covered on all sides. By applying the correct dosage of fluid a protective layer is formed with a thickness sufficient to protect the core sample from low-intensity parts of the ion beam, while it is sufficiently thin to be easily milled by the high-intensity part of the beam. Also interaction of core material with scattered ions or electrons is eliminated or at least greatly reduced.

Figure 8:
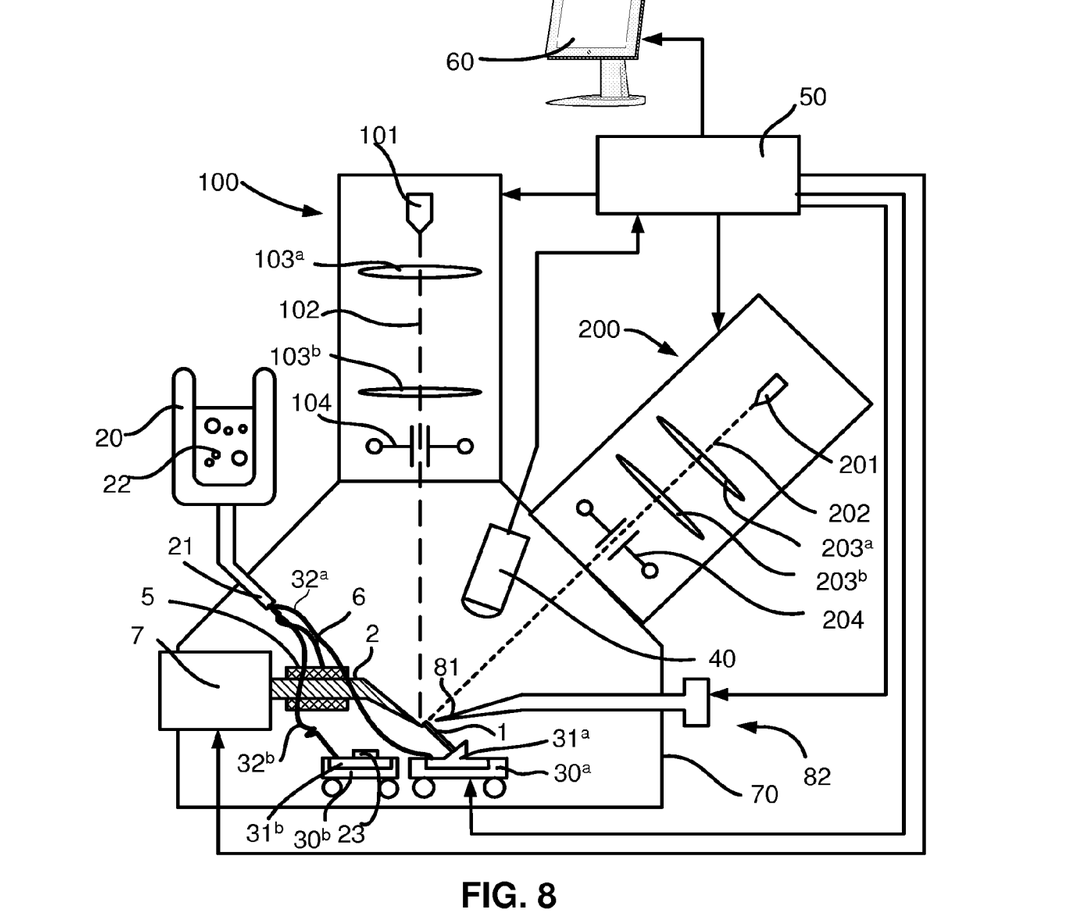

FIG. 8 schematically shows an apparatus to slice a lamella from a core and deposit it on a sample carrier.

FIG. 8 can be thought to be derived from FIG. 5. It differs in that the stage 30 is split in two different stages, stage 30$^a$ and stage 30$^b$, which can be moved independently. Stage 30 now has a rotation axis perpendicular to the ion beam column 200, so that the ion beam can form a flat surface on the sample 1 in the form of a core and slice lamella from the core. Further a gas injection system 82 is added, with a nozzle 81 directed to the core, so that the core can be covered with a protective layer by directing gas from the nozzle while rotating the core. Manipulator 2 can be attached to the lamella sliced from the core, after which the lamella can be attached to a sample carrier 23 such as a TEM grid placed on stage 30$^b$.

The invention claimed is:

1. A method for extracting a sample from a substrate and attaching the sample to a manipulator, the method comprising the steps of:
    freeing at least partly a sample from a substrate;
    contacting the sample with the manipulator;
    attaching the sample to the manipulator; and
    removing the sample from the substrate;
wherein
    the sample is a frozen sample;
    the sample is attached to the manipulator by heating at least the part of the sample in contact with the manipulator, thereby causing a phase change of part of the sample material, and
    subsequent freezing said part of the sample in contact with the manipulator to the manipulator, thereby forming a bond between the sample and the manipulator.

2. The method according to claim 1 in which the sample comprises water.

3. The method according to claim 2 in which the sample is a vitrified sample.

4. The method according to claim 1 in which the method further comprises separating the sample from the manipulator by heating at least the part of the sample in contact with the manipulator.

5. The method according to claim 1 in which the heating is caused by heating with a focused beam of light.

6. The method according to claim 1 in which the heating is caused by heating with a beam of energetic particles.

7. The method according to claim 1 in which the heating of the sample is caused by the temperature of the part of the manipulator in contact with the sample, said temperature of the manipulator at the moment of phase change being above the temperature at which the phase change occurs.

8. The method according to claim 7 in which the temperature of the part of the manipulator in contact with the sample is changed by electrical heating of said part.

9. The method according to claim 1 in which part of the manipulator is kept at a temperature below the freezing point of the sample material.

10. The method according to claim 1 in which the method is performed in vacuum.

11. The method according to claim 1 in which the method further comprises inspection and/or analysis of the sample using an energetic beam of charged particles.

12. The method according to claim 11 in which the phase change of the sample is restricted to an area of the sample outside the area to be inspected and/or analysed.

13. The method according to claim 1 in which the freeing of the sample involves focused ion beam milling.

14. The method according to claim 13 in which freeing the sample comprises slicing a lamella from a frozen core, the lamella representing a cross-section of said core.

15. The method according to claim 14 in which, prior to slicing the lamella from the core, the core is covered with a protective layer.

16. The method according to claim 15 in which the core is covered with a protective layer by directing a jet of gas to the core while rotating the core with respect to the jet of gas.

17. The method according to claim 14 in which the core is formed by high-pressure freezing of a hydrated material, resulting in a vitreous core.

18. An apparatus for forming samples from a cryogenic hydrated substrate and attaching the samples to a manipulator, the apparatus comprising:
    a column equipped to produce a focused ion beam on a sample position,
    a stage for holding the substrate equipped to position the substrate, in which at least the part of the stage equipped to be in contact with the substrate is equipped to be cooled to a cryogenic temperature,
    a manipulator showing an extremity to which extremity a sample may be attached, the extremity of the manipulator equipped to be held at a cryogenic temperature,
wherein
    the extremity of the manipulator is equipped to be heated to a temperature above the melting temperature or sublimation temperature of water while another part of the manipulator is held at a cryogenic temperature.

19. The apparatus of claim 18 in which the apparatus further comprises a gas injection system to direct a jet of gas to the sample position.

20. The apparatus according to claim 18 in which the substrate is a core and the apparatus is further equipped with a programmable control unit controlling the apparatus in such a way that the apparatus is equipped to automatically:

position the core to a cutting position,
cover the core with a protective coating by directing a jet of fluid to the core,
slice the core, thereby forming a lamella from the core,
connect the extremity of the manipulator to the lamella to transport it to a sample carrier, and
release the lamella on the sample carrier.

* * * * *